(12) United States Patent
Kuhn

(10) Patent No.: US 6,183,457 B1
(45) Date of Patent: Feb. 6, 2001

(54) TAMPON AND THE METHOD FOR PACKAGING SAME

(75) Inventor: Kurt Kuhn, Windlach (CH)

(73) Assignee: Ruggli Projects AG (CH)

( * ) Notice: Under 35 U.S.C. 154(b), the term of this patent shall be extended for 0 days.

(21) Appl. No.: 09/334,048

(22) Filed: Jun. 15, 1999

(30) Foreign Application Priority Data

Jun. 15, 1998 (DE) ............................................. 198 26 541

(51) Int. Cl.[7] .............................. A61F 13/15; B65D 81/24
(52) U.S. Cl. ................... 604/385.18; 604/904; 206/210; 206/361
(58) Field of Search ............................... 604/904, 385.17, 604/385.18, 363; 206/210, 361, 363, 440

(56) References Cited

U.S. PATENT DOCUMENTS

| | | |
|---|---|---|
| 3,863,636 | 2/1975 | Johnson . |
| 4,648,867 * | 3/1987 | Conner et al. .................... 604/14 |
| 4,743,237 | 5/1988 | Sweere . |
| 4,775,377 | 10/1988 | Sweere . |
| 4,923,440 * | 5/1990 | Genaro ................................ 604/14 |

FOREIGN PATENT DOCUMENTS

| | | |
|---|---|---|
| 1 157 733 | 11/1963 | (DE) . |
| 26 46 772 | 4/1978 | (DE) . |
| 88 02 553 | 5/1988 | (DE) . |
| 296 20 118 U1 | 4/1998 | (DE) . |

* cited by examiner

*Primary Examiner*—Dennis Ruhl
(74) *Attorney, Agent, or Firm*—Robert W. Becker & Associates

(57) ABSTRACT

A tampon has a cylindrical base body having a rounded or conical leading end and a rearward end having an end face. A string having one end fastened within the cylindrical base body and having a main string portion protruding from the end face is provided. A removable protective sleeve encloses the cylindrical base body and the main string portion and has an end portion covering the end face. The main string portion is arranged completely at the end face when the protective sleeve encloses the cylindrical base body and the string. The main string portion has a string end resting at the end portion of the sleeve, wherein the string end is materially connected to the sleeve end portion. A method for packaging the inventive tampon is disclosed.

7 Claims, 1 Drawing Sheet

TAMPON AND THE METHOD FOR PACKAGING SAME

BACKGROUND OF THE INVENTION

The present invention relates to a tampon, especially for female hygiene, comprised of a substantially cylindrical base body with a leading end in the direction of insertion that is rounded or conical as well as a rearward end with an end face from which protrudes a portion of a string or band that with part of its length is fastened within the base body. The base body and the string are enclosed by a protective sleeve which is to be removed before using the tampon. The invention furthermore relates to a method for packaging the tampon.

Known tampons are comprised of a fiber fleece material which is brought into the desired afore-disclosed shape by suitable pressing tools. The known tampons differ primarily with respect to their shape, holding capability, and their absorption rate. The latter is determined by the absorption speed as well as the fluid receiving capacity of the tampon. A uniform and high liquid absorption capacity depends on the effective surface of the tampon. In order not to affect the absorption capacity of the tampon after manufacture by storing and transporting, it is conventional to provide a protective sleeve that is usually made of cellophane.

The known tampons of the aforementioned type have the disadvantage that the string for pulling out the tampon is pressed into the fiber structure of the tampon during the step of enclosing the tampon with the substantially air and moisture-tight protective sleeve. Since a tampon is conventionally used with extended string, it is necessary to remove the string before use from its position pressed into the fiber structure. This not only entails the risk of damaging the fiber structure, for example, by fingernails, thus causing a detrimental effect on the absorption capacity of the tampon, but also is undesirable with respect to hygienic aspects.

It is therefore an object of the present invention to provide a tampon with improved handling properties and also a method for packaging such tampon.

SUMMARY OF THE INVENTION

According to the present invention, the main string portion of the string that is guided out of the base body is arranged completely in the area of the end face when the tampon is enclosed by the protective sleeve, whereby an end portion of the string resting at the end portion of the protective sleeve at the end face of the tampon is materially connected to the protective sleeve.

The term materially connected refers to bonding or fusing or welding two materials to one another so that the two materials are intimately and inseparably bonded.

In a tampon embodied accordingly, it is no longer required to grip the string directly in order to extend it for use. This is so because the main string portion extending from the base body is removed and stretched upon removing of the end portion of the protective sleeve that covers the rearward end face. This is possible because the string portion exterior to the base body is positioned only within the area of the rearward end face while the protective sleeve is still enclosing the tampon and is only placed at the end face of the tampon in a lose attachment for temporarily securing the string thereat. Upon removal of the end portion of the protective sleeve from the rearward end face, the main portion of the string projecting from the base body is then removed forcibly from the tampon because the end portion of the main string portion is materially connected to the protective sleeve. The string is thus stretched and extended whereby, only upon surpassing a certain pulling force, the material connection between the string and the protective sleeve will rupture. A complicated and difficult removal of the string by fingernails is thus no longer required so that the inventive tampon has improved handling properties.

Accordingly, gripping the string, as is known from the prior art tampons, is no longer necessary so that, in addition, the risk of damage to the surface of the tampon, especially removal of portions of the fiber composite, for example, by fingernails is avoided. In this manner, a potentially damaging deposit of fiber composite material, removed from the tampon, within the body orifice after use is thus reliably prevented.

In order to provide for a simple and reliable material connection of the end portion of the main string portion and the end portion of the protective sleeve covering the rearward end face, according to an advantageous embodiment of the invention it is suggested that the end portion of the protective sleeve covering the rearward end face is connected by thermal fusing to the end portion of the string resting thereat. According to a further feature of the invention a tear tab is provided for the removal of the protective sleeve. It is preferably positioned about the circumference of the tampon approximately at half the length of the tampon. This has the advantage that, after tearing open the protective sleeve by the tear tab, the protective sleeve is thus divided into two substantially sleeve-shaped portions whereby one of these sleeve portions covers the leading end and the other of these sleeve portions covers the opposed rearward end of the tampon. By actually pulling apart these two portions, whereby at the same time the main string portion connected to the rearward end face of the tampon is also stretched, the protective sleeve can thus be easily removed from the tampon without the risk of damaging it.

Inventively, the method for packaging a tampon as disclosed above is characterized by the method steps of:

a) loosely attaching the main string portion of the string extending from the cylindrical base body of the tampon in the area of the rearward end face at the tampon for temporarily securing the position of the string;

b) completely enclosing the tampon, including the loosely attached string, by a protective sleeve;

c) materially connecting the end portion of the protective sleeve at the rearward end face of the tampon to the end portion of the string resting thereat.

With such a method the inventive tampon can be manufactured. This is so because the end portion of the main string portion extending from the tampon is loosely attached (temporarily secured) in the area of the rearward end face for securing the string thereat and, subsequently, the end portion of the protective sleeve covering the rearward end face of the tampon is materially connected to the end portion of the main string portion. In this manner, upon removal of the protective sleeve, the main string portion of the string extending from the base body is simultaneously stretched and extended and removed from the end face of the tampon.

It is especially advantageous when the end portion of the protective sleeve covering the rearward end face of the tampon is connected by thermal fusing to the end portion of the string resting at the end face, whereby the required heat energy is provided by a heat source positioned opposite the rearward end face. This ensures a safe attachment of the end portion of the string to the protective sleeve during removal of the protective sleeve, especially to such an extent that the string will be completely extended and only thereafter, when a certain pulling load is exerted, will be separated from the protective sleeve. This arrangement of the heat source allows for a pointed thermal fusing without affecting other portions of the protective sleeve. A further advantage is that the fusing of the protective sleeve and the string also closes off or seals the protective sleeve substantially air and moisture tight at the rearward end.

With respect to an advantageous method, it is furthermore suggested that the effective exposure time of the heat source is 0.2 s to 1.5 s at a temperature of the employed heating element between 80° C. and 250° C.

In order to provide for a simple manipulation of the tampon, it is furthermore suggested to provide the protective sleeve with a tear tab.

BRIEF DESCRIPTION OF THE DRAWINGS

The object and advantages of the present inventions will appear more clearly from the following specification in conjunction with the accompanying drawings, in which:

FIG. 2a shows a view of the uncovered rearward end of the tampon according to FIG. 2;

FIG. 3a shows a view of the rearward end of the tampon according to FIG. 2 covered by the protective sleeve;

DESCRIPTION OF PREFERRED EMBODIMENTS

Figure 1:
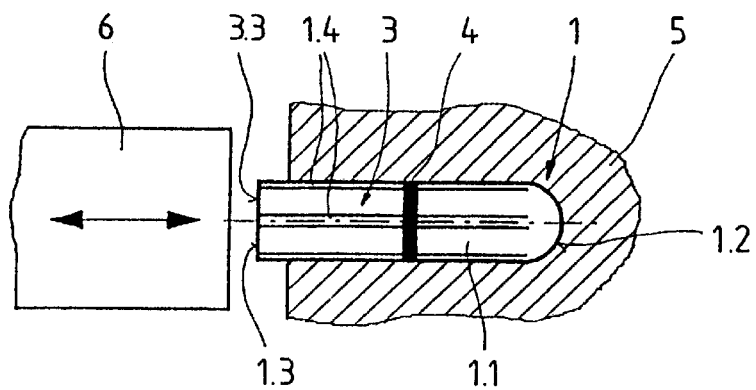
FIG. 1 is a schematic representation of fusing the protective sleeve of a tampon by a heat source positioned opposite the rearward end face of the tampon.

The present invention will now be described in detail with the aid of several embodiments utilizing FIGS. 1 through 5.

The tampon 1 illustrated in FIGS. 1 through 5 is comprised of a substantially cylindrical base body 1.1 which has a rounded or conical end 1.2 in the insertion direction and has a rearward planar end face 1.3. A main string portion 2 of a string, which is connected with a portion thereof within the base body 1.1, projects from the rearward face 1.3 as can be seen especially in FIGS. 4 and 5. While the tampon 1 is comprised of fiber fleece material that is pressed into the desired shape, the string is comprised of cotton or viscose staple fiber. The base body 1.1 is also provide in the longitudinal direction with ribs 1.4.

Figure 2:
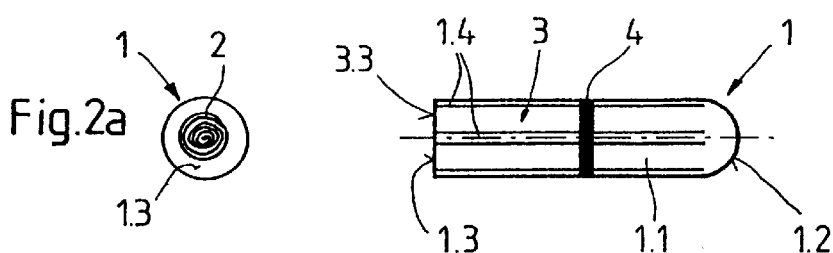
FIG. 2 shows a side view of a tampon enclosed by a fused protective sleeve showing the tear tab in its initial position.
Figure 3:
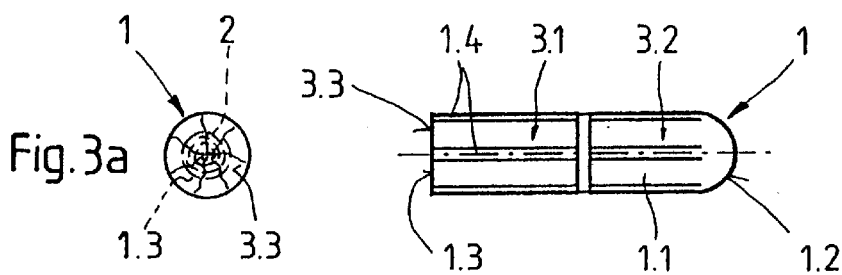
FIG. 3 shows a side view of the tampon according to FIG. 2 with the tear tab removed.

The tampon which is represented in FIGS. 1 through 3 is surrounded by a protective sleeve 3 which is comprised of a substantially sleeve-shaped rearward portion 3.1, which surrounds the rearward end with the end face 1.3 of the tampon 1, and a substantially sleeve-shaped forward end portion 3.2, which surrounds the forward end 1.2 of the tampon 1. At approximately half the length of the tampon 1 the inner side of the protective sleeve 3 is provided with a tear tab 4 extending about the circumference of the tampon 1. The protective sleeve 3 as well as the tear tab 4 are comprised of a transparent foil, for example, cellophane. Alternatively, the protective sleeve 3 and the tear tab 4 can also be comprised of polypropylene.

For packaging the tampon 1 in the protective sleeve 3, in a first step a main string portion 2 of the string projecting from the base body 1.1 is loosely gathered and attached in the area of the rearward end face 1.3 of the tampon 1, as can be seen especially in FIGS. 2a and 3a. Subsequently, the tampon 1 including the loosely attached main string portion 2 are completely enclosed by the protective sleeve 3. Finally, the end portion 3.3 of the rearward sleeve portion 3.1 of the protective sleeve 3 covering the rearward end face 1.3 of the tampon is fused and in this manner is also simultaneously connected (materially connected) to the end portion of the main string portion 2 resting thereat. The thermal fusing of the end portion 3.3 covering the end face for closing and sealing the protective sleeve 3 and for connecting it to the main string portion 2 is represented in FIG. 1. It can be seen that the tampon 1 is positioned in a blind bore-like receiving element 5 which encloses the tampon 1 with the exception of the rearward end and the rearward end face 1.3. Opposite the rearward end face 1.3, a heating element 6, which is indicated symbolically by the double arrow in FIG. 1, is arranged with which the end portion 3.3 of the protective sleeve 3 covering the rearward end face 1.3 of the tampon is pointedly heated. For an effective heating period of 0.2 seconds to 1.5 seconds the temperature is between 80° C. and 250° C.

Figure 4:
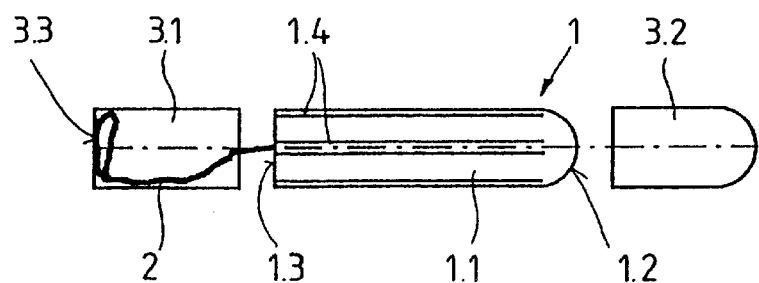
FIG. 4 shows a side view of the tampon according to FIG. 3 with the protective sleeve pulled apart.
Figure 5:
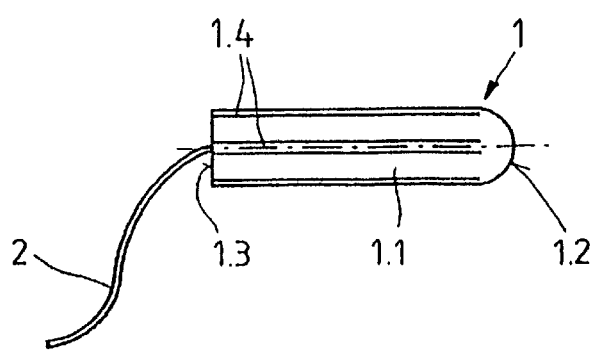
FIG. 5 shows a side view of the tampon according to FIG. 4 with completely removed protective sleeve and freely extending string.

In FIGS. 2 and 2a as well as 3 and 3a, the tampon 1 provided with the protective sleeve 3 in the aforementioned manner is shown. In the state represented in FIG. 2, the tear tab 4 is still attached to the protective sleeve 3 between the forward sleeve portion 3.2 and the rearward sleeve portion 3.1 of the protective sleeve 3 so that the tampon 1 is substantially sealed in an airtight and moisture tight manner. The state represented in FIG. 3 shows the tear tab 4 being removed. The forward sleeve portion 3.2 as well as the rearward sleeve portion 3.1 of the protective sleeve 3 can be removed only in opposite axial directions from the tampon 1, as can be seen in FIG. 4. Advantageously, first the rearward sleeve portion 3.1 of the protective sleeve 3 is removed and, during this removal, the tampon 1 is held at the forward sleeve portion 3.2 of the protective sleeve 3. In this manner a premature manual handling of the tampon 1 is avoided so that the tampon 1 is protected against damage and soiling. In this context, it is also important that upon removal of the rearward sleeve portion 3.1 of the protective sleeve 3, the sleeve portion 3.3 of the protective sleeve 3 covering the rearward end face 1.3 of the tampon, which is connected to the end portion of the main string portion 2, will stretch the main string portion 2 of the string so that the string is unfolded from the tampon 1. Once the main string portion 2 is completely stretched, the connection between the main string portion 2 and the end portion 3.3 of the protective sleeve 3 will be separated from one another because of the resulting pulling forces so that the string, as can be seen especially in FIG. 5, extends freely.

The inventive tampon as well as the inventive method for packaging will result in improved handling properties of the tampon. An end portion of the main string portion 2 is connected to the protective sleeve 3, so that by removing the protective sleeve 3 the string 2 protruding from the base body 1.1 of the tampon is unfolded and stretched away from the tampon base body. A complicated and difficult manual removal of the string 2 from the tampon is eliminated. Furthermore, in this manner the tampon 1 is protected against damage because no fiber composite portions will be removed.

The specification incorporates by reference the disclosure of German priority document 198 26 541.7 of Jun. 15, 1998.

The present invention is, of course, in no way restricted to the specific disclosure of the specification and drawings, but also encompasses any modifications within the scope of the appended claims.

What is claimed is:

1. A tampon comprising:

a cylindrical base body (1.1) having a rounded or conical leading end (1.2) and a rearward end having an end face (1.3);

a string having a first string end fastened within said cylindrical base body (1) and having a main string portion (2) protruding from said end face (1.3);

a removable protective sleeve (3) enclosing said cylindrical base body (1) and said main string portion (2) and having an end portion (3.3) covering said end face (1.3);

said string (2) arranged completely at said end face (1.3) when said protective sleeve (3) encloses said cylindrical base body (1) and said string (2);

said main string portion (2) comprising a second string end resting at said end portion (3.3), wherein said second string end is materially connected to said end portion (3.3).

2. A tampon according to claim 1, wherein said second string end is thermally fused to said end portion (3.3).

3. A tampon according to claim 1, wherein said removable protective sleeve (3) has a tear strip (4) extending about a circumference of said base body (1) and positioned centrally relative to a length of said base body.

4. A method for packaging a tampon of claim 1, said method comprising the steps of:

a) loosely securing said main string portion at said end face (1.3) of said cylindrical base body (1);

b) completely enclosing said cylindrical base body (1) and said main string portion (2) in said removable protective sleeve (3);

c) materially connecting said second string end of said main string portion (2) to said end portion (3.3) of said removable protective sleeve (3).

5. A method according to claim 4, wherein in said step c) said second string end is thermally fused to said end portion (3.3) by a heat source (6) positioned opposite said end face (1.3).

6. A method according to claim 5, wherein said step c) includes applying heat for 0.2 s to 1.5 s by a heating element of said heat source (6) at a temperature of 80° C. to 250° C.

7. A method according to claim 4, wherein said step b) includes providing said removable protective sleeve (3) with a tear tab (4).

* * * * *